(12) United States Patent
Boesen

(10) Patent No.: US 9,205,193 B2
(45) Date of Patent: Dec. 8, 2015

(54) SELF-CONTAINED MEDICATION INJECTION SYSTEM AND METHOD

(76) Inventor: Peter V. Boesen, Des Moines, IA (US)

(*) Notice: Subject to any disclaimer, the term of this patent is extended or adjusted under 35 U.S.C. 154(b) by 544 days.

(21) Appl. No.: 11/761,861

(22) Filed: Jun. 12, 2007

(65) Prior Publication Data

US 2008/0312604 A1 Dec. 18, 2008

(51) Int. Cl.
*A61M 5/20* (2006.01)
*A61M 5/00* (2006.01)
*A61M 5/315* (2006.01)

(52) U.S. Cl.
CPC ............ *A61M 5/2033* (2013.01); *A61M 5/008* (2013.01); *A61M 5/31546* (2013.01); *A61M 2005/004* (2013.01); *A61M 2005/206* (2013.01); *A61M 2205/35* (2013.01); *A61M 2205/502* (2013.01); *A61M 2205/52* (2013.01); *A61M 2205/581* (2013.01); *A61M 2205/609* (2013.01)

(58) Field of Classification Search
CPC ................ A61M 2005/004; A61M 2005/206; A61M 2205/35; A61M 2205/502; A61M 2205/52; A61M 2205/581; A61M 2205/609; A61M 5/008; A61M 5/2033; A61M 5/31546
USPC ........... 604/125, 187, 19, 207, 208, 209, 210, 604/211, 246, 264, 272, 506, 65, 66, 67, 604/173, 181
See application file for complete search history.

(56) References Cited

U.S. PATENT DOCUMENTS

| | | | |
|---|---|---|---|
| 4,531,437 A | 7/1985 | Szablak et al. | |
| 4,995,871 A | 2/1991 | Sasaki et al. | |
| 5,645,534 A | 7/1997 | Chanoch | |
| 5,968,021 A | 10/1999 | Ejlersen | |
| 6,393,404 B2 | 5/2002 | Waters et al. | |
| 6,585,698 B1* | 7/2003 | Packman et al. | 604/207 |
| 7,014,069 B2 | 3/2006 | Crosnier et al. | |
| 7,169,132 B2 | 1/2007 | Bendek et al. | |
| 7,361,163 B2* | 4/2008 | Cohen | 604/232 |
| 2002/0020646 A1* | 2/2002 | Groth et al. | 206/366 |
| 2004/0122355 A1* | 6/2004 | Langley et al. | 604/67 |
| 2004/0162521 A1* | 8/2004 | Bengtsson | 604/136 |
| 2004/0260270 A1* | 12/2004 | Cohen | 604/506 |
| 2006/0015066 A1* | 1/2006 | Turieo et al. | 604/136 |
| 2006/0213249 A1* | 9/2006 | Uram et al. | 73/1.36 |
| 2006/0229570 A1* | 10/2006 | Lovell et al. | 604/218 |
| 2007/0203458 A1* | 8/2007 | Tsubota | 604/198 |
| 2007/0244428 A1* | 10/2007 | Uram et al. | 604/67 |
| 2010/0036362 A1* | 2/2010 | Slate et al. | 604/506 |

FOREIGN PATENT DOCUMENTS

WO WO 2005077441 A2 * 8/2005

OTHER PUBLICATIONS

Byetta Quick Start Guide, 2006 Amylin Pharmaceuticals, Inc. and Eli Lilly and Company, 02-06-3196-A; 4 pages.
"The LANTUS® SoloSTAR® Insulin Pen" http://www.lantus.com/solostar/solostar_insulin_pen.aspx, printed Jun. 15, 2010, 2 pages.
"Huma-Pen Memoir for diabetics", www.ubergizmo.com/2007/02/huma-pen-memoir-for-diabetics, 2 pages, printed Internet Jul. 13, 2011.

* cited by examiner

*Primary Examiner* — Imani Hayman
(74) *Attorney, Agent, or Firm* — McKee, Voorhees & Sease, PLC

(57) ABSTRACT

A self-contained system for medication injection is activated by the user, who is able to distribute the medication through the self-contained needle system for intradermal or intramuscular application of the medication. The self-contained system may be a medication delivery pen having a pen body assembly comprising a distal end, a proximal end and a needle array containing a plurality of needles disposed within the pen body assembly.

42 Claims, 8 Drawing Sheets

SELF-CONTAINED MEDICATION INJECTION SYSTEM AND METHOD

BACKGROUND OF THE INVENTION

Health care costs are rapidly escalating, with the combined issues of an aging population here in the United States and elsewhere, as well as the increased prevalence of chronic disease states such as diabetes mellitus and asthma. Many of these disease states are now being effectively treated on an outpatient basis. Unfortunately, this places a greater emphasis on patient compliance to achieve satisfactory outcomes. Diseases such as insulin dependent diabetes mellitus, and insulin resistant diabetes mellitus, to name but two, frequently utilize injectable medications to stabilize the patient. Injectable medications include insulin, as well as other types of medications such as incretin mimetics, the first of which in the class is labeled Byetta.

In order to effectively control many disease states, the repeated application of injectable medications is required. Many patients are quite resistant to such applications, and as a consequence, the disease state is less controlled than is optimal. Issues principally stem from compliance with following the drug schedule, especially if it is required one or more times each day. This problem is further compounded by the need for injection of the medication. Many patients resist injections due to the fear of pain, difficulty with manipulation of the needles, discomfort at the injection site, and the need to properly purchase, and dispose of the needle and container after use is completed. Further, with the advent of such communicable diseases such as HIV, or Hepatitis C, the risk of exposed needles to others is increased. What is needed is an improved self-contained medication injection system.

Therefore, it is a primary object, feature or advantage of the present invention to improve upon the state of the art.

It is a further object, feature, or advantage of the present invention to provide a self-contained medication injection system incorporating built in needles, so that the user is not required to dispose of the expended materials.

Yet another object, feature, or advantage of the present invention is to provide a system that is wholly contained, eliminating the need to place and replace needles into the system with each usage.

Still another object, feature or advantage of the present invention is to provide a method for delivery of a drug where the user, or other health care workers are protected from inadvertent contact with the needle.

Still a further object, feature or advantage of the present invention is to provide a system for monitoring temperature of the medication to be dispensed, and to provide a warning if such parameters are breached.

Still yet another object, feature or advantage of the present invention is to provide a communication link from the device that requires very low power.

It is a further feature of the present invention to incorporate a wireless link for communication to an electronic device that records data such as dosing information and distributions, or receiving updates from the electronic device.

These and/or other objects, features or advantages of the present invention will become apparent from the specification and claims.

BRIEF SUMMARY OF THE INVENTION

The present invention relates to a self-contained medication delivery device, such as an injection system for administration of intramuscular or intradermal medications. In one embodiment of the present invention, the needle system is wholly contained in the device, and is mechanically moved into position for administration of the medication. The needle is wholly contained initially within the device. Upon initiating the system for medication administration, the needle is moved into the appropriate position for injection. The needle system can then be advanced outward from the device either before the injection of the medication, or in conjunction with the distribution of the medication. After the injection of the medication, the needle is then retracted back into the body of the self-contained medication delivery device, preventing unwanted contact with the patient or others. Storage of all needles used in injection is facilitated within the device, segregating the used needles from the unused ones. In the electromechanical system, sensors and/or small motors may facilitate the needle control system, as well as monitor various parameters of the administration of the medication. These parameters may include such variables as time of administration, dose administered, skin temperature or ambient temperature at the time of administration, failure of dosing or of the needle advance/retract system, location of the administration on the body, geographic location of the administration, among other parameters. Storage of data is contemplated, with the capability for wireless transmission to a receptor device. Although the present invention also provides for sensing at the injection site, a plurality of sensors is also postulated to monitor other parameters. Linkage of the device through a low power communication link is postulated. The use of a low power communication link such as Bluetooth, or Ultra Wideband (UWB) allows for reductions in transmit power required and for greater bandwidth applications between the self-contained medication delivery device, and the linked electronic device.

According to one aspect of the present invention, a medication delivery pen is disclosed. The medication delivery pen includes a pen body assembly comprising a distal end, a proximal end and a needle array containing a plurality of needles disposed within the pen body assembly.

According to yet another aspect of the present invention, a medication delivery pen includes a pen body assembly comprising a distal end, a proximal end, a needle array containing a plurality of needles, and a needle assembly adapted to convey clean needles of the needle array towards the proximal end of the pen body assembly for delivering medication via injection.

According to another aspect of the present invention, a method for delivery of medication includes providing a self-contained medication injection system containing a plurality of needles and adapted for concurrently storing both a plurality unused needle and a plurality of used needles and reporting information about delivery of medication using the self-contained injection system.

According to yet another aspect of the present invention, a medication delivery pen is provided. The medication delivery pen includes a pen body assembly comprising a distal end, a proximal end, a reservoir of medication disposed within the pen body, a needle operative connected to the pen body assembly for delivering the medication to a user, and at least one sensor on the pen body assembly, and a short range transceiver operatively connected to the at least one sensor and disposed within the pen body assembly for reporting information associated with use of the medication delivery pen.

DETAILED DESCRIPTION OF THE PREFERRED EMBODIMENT

The present invention relates to a self-contained medication delivery device, such as an injection system for administration of intramuscular or intradermal medications. To assist in describing the invention various embodiments of the invention are described. It is to be understood that the scope of the invention is not to be limited to the specific embodiments described. It is also to be understood that various features or structures of the various embodiments may be combined together where appropriate to do so.

In one embodiment of the present invention, the needle system is wholly contained in the device, and is mechanically moved into position for administration of the medication. The needle is wholly contained initially within the device. Upon initiating the system for medication administration, the needle is moved into the appropriate position for injection. The needle system can then be advanced outward from the device either before the injection of the medication, or in conjunction with the distribution of the medication. After the injection of the medication, the needle is then retracted back into the body of the self-contained medication delivery device, preventing unwanted contact with the patient or others. Storage of all needles used in injection is facilitated within the device, segregating the used needles from the unused ones. In the electromechanical system, sensors and/or small motors would facilitate the needle control system, as well as monitor various parameters of the administration of the medication. These parameters could be such variables as time of administration, dose administered, skin temperature or ambient temperature at the time of administration, failure of dosing or of the needle advance/retract system, location of the administration on the body, geographic location of the administration, among other parameters. Storage of data is contemplated, with the capability for wireless transmission to a receptor device. Although the present invention also provides for sensing at the injection site, a plurality of sensors is also postulated to monitor other parameters. Linkage of the device through a low power communication link is postulated. The use of a low power communication link such as Bluetooth, or UWB allows for reductions in transmit power required and for greater bandwidth applications between the self-contained medication delivery device, and the linked electronic device.

It should be understood that when describing the invention, the term "user" is used to refer to either a person administering or overseeing or observing the administration of medication and/or the person receiving the injection. Although, often times the "user" may be self-administering the medication, this is not necessarily so, so the term "user" is not to be limited to such instances.

Figure 1:
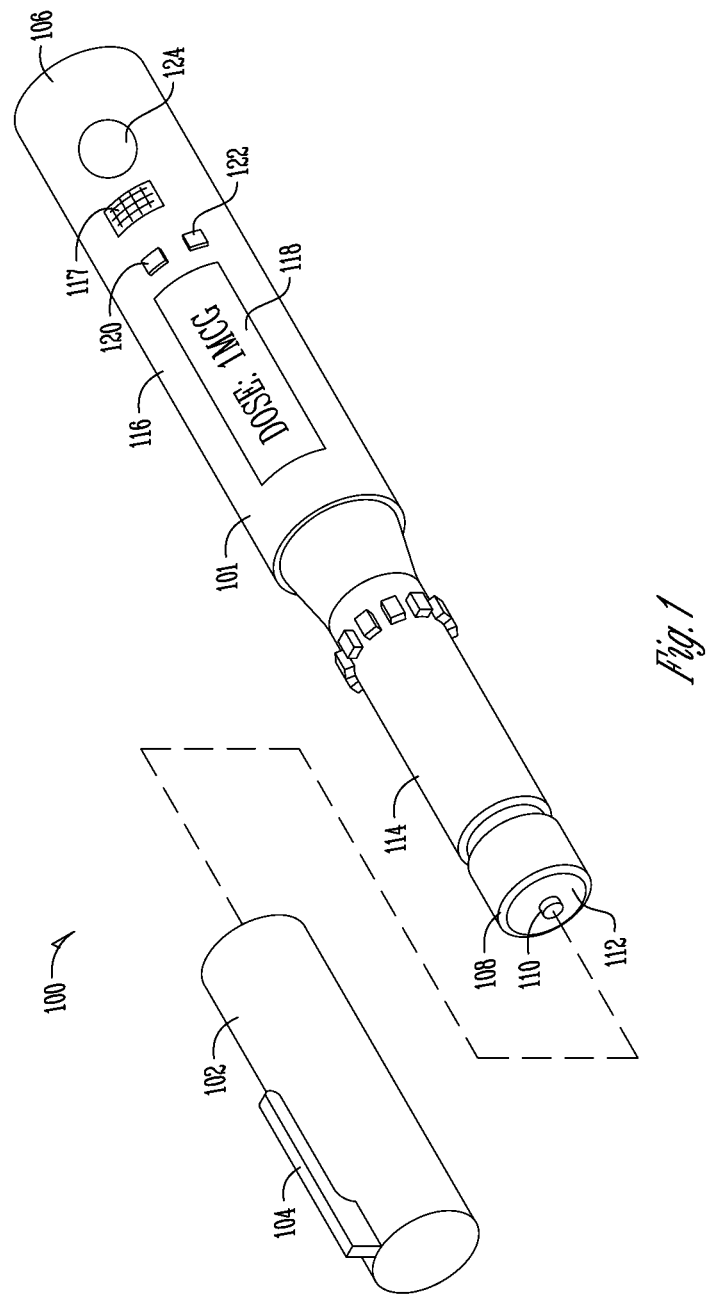
FIG. 1 is a perspective view of a self-contained medication device such as a medication delivery pen according to one embodiment of the present invention.

FIG. 1 is a pictorial representation of a self-contained medication device according to one embodiment of the present invention. In FIG. 1, a medication delivery pen 100 is shown. The medication delivery pen 100 has a pen body assembly 101 having a distal end 106 and a proximal end 108. The medication delivery pen 100 may also include a pen cap 102 with clip 104. A bore 110 is shown in skin contact area 112. One or more sensors may be at the skin contact area 112. When actuated, such as by activation of button 124, a needle extends from bore 110 for delivery of medication.

A display 118 is shown on the pen body assembly 101. The display 118 can be used for displaying dosage settings or information based on sensor readings such as, but not limited to, skin temperature, or temperature of the medication. In addition, the display 118 may display information that assists the user with administering the medication. For example, the display 118 may indicate that additional skin contact pressure may need to be applied based on sensor information. The display 118 may provide information helpful in determining a proper dosage setting. The display 118 may also include time and date information. The display 118 may also indicate the amount of medication left or that additional medication is required. The display 118 may also allow for loading of specific patient information such as e-mails or phone numbers to call if a dose is missed, indicate the number of needles left or indicate that new needles are required. The display 118 may also display historical information that has been stored such as information regarding the time of prior injections, the dosage of prior injections, or other information. A speaker 117 is shown. Verbal cues, warnings or confirmations can be distributed to the user.

User inputs such as buttons 120, 122 are shown. The user input buttons 120, 122 may be used to increase or decrease dosage settings, cycle between display modes, or make selections, such as by holding one of the buttons for a longer period of time, or depressing both buttons simultaneously. Additional user inputs may also be used where desirable, such as where greater functionality is imparted to the device. In addition, buttons 120, 122 and display 118 may be of different configurations and may be placed at different locations.

Figure 2:
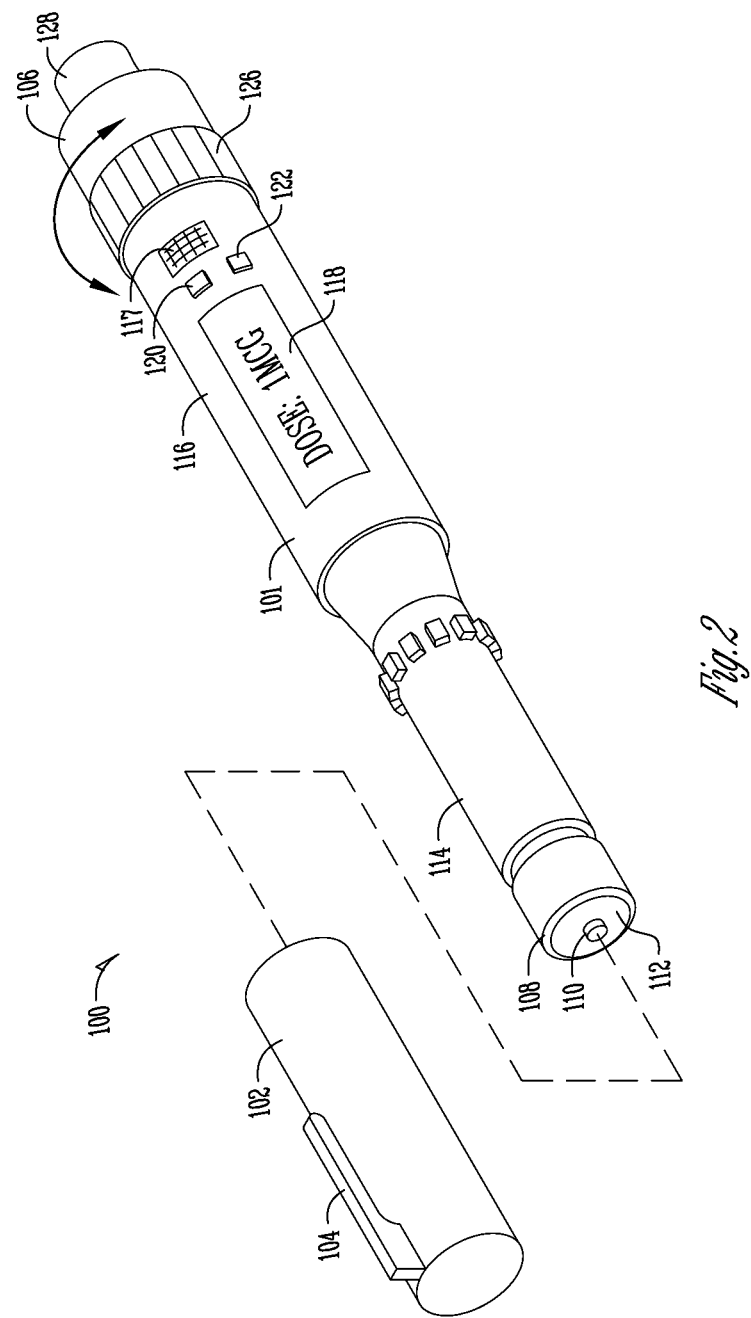
FIG. 2 is a perspective view of a medication delivery pen according to another embodiment of the present invention.

FIG. 2 is a pictorial representation of a self-contained medication device according to another embodiment of the present invention. The device shown in FIG. 2 is similar to the device shown in FIG. 1, however, instead of using an electronic system to control dosage, a dose setting 126 which includes a dial is provided. In addition, to activate delivery of a dose of the medication, an activation input 128 is shown which may be mechanical or electromechanical.

Figure 3:
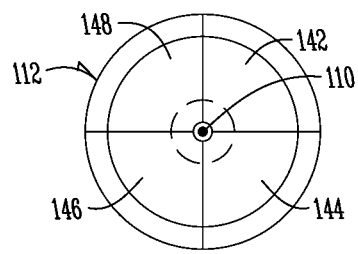
FIG. 3 is an end view illustrating one embodiment of the skin contact area of a medication delivery pen.

FIG. 3 illustrates one embodiment of the skin contact area 112. The skin contact area 112 surrounds a bore 110 through which a needle extends in order to deliver medication. Sensors 142, 144, 146, and 148 are shown. The sensors 142, 144, 146, 148 may be of various types to serve various purposes. For examples, sensors 144, 148 may be contact sensors or pressure sensors. Information obtained from sensors 144, 148 may be used to determine if sufficient pressure is being applied to the skin for the needle to properly deliver medication. If insufficient pressure is being applied, an audible and/or visual warning may be given to the user, or where electronic activation is used, it may be disabled until proper pressure is applied. Speaker 117 may be utilized to provide feedback. As sensors 144, 148 are opposite of one another, information can also be used to determine angle of entry of a needle. Sensor 146 and/or sensor 142 may be temperature sensors for determining skin temperature of the user being injected. Pore 110 could also utilize a separate clean needle array to assay physiologic parameters such as blood glucose, before a dose is readied for injection.

Figure 4:
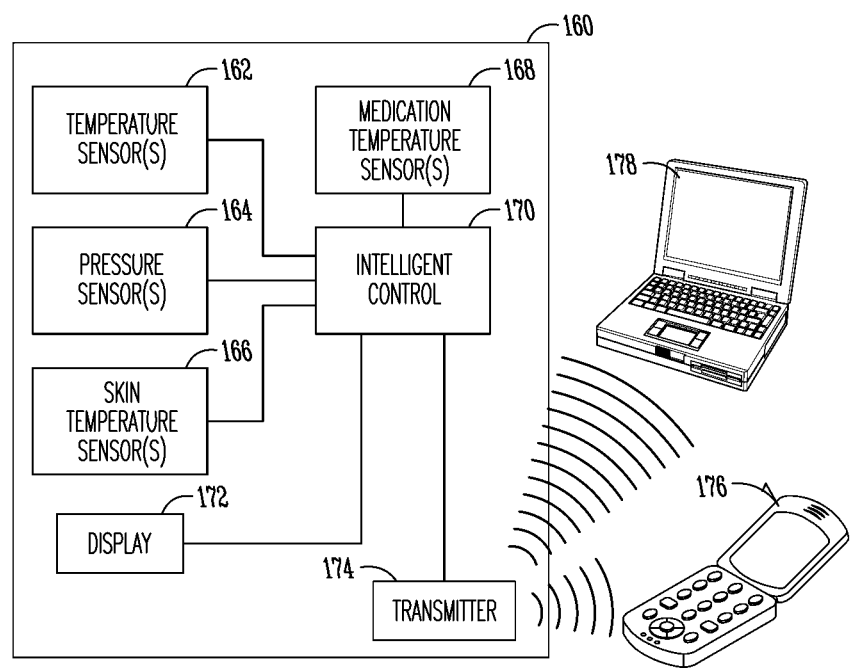
FIG. 4 is a block diagram illustrating one embodiment of a self-contained medication device such as a medication delivery pen.

FIG. 4 is a block diagram illustrating one embodiment of the present invention. A pen 160 is shown. The pen 160 includes one or more temperature sensors 162, one or more contact or pressure sensors 164, one or more skin temperature sensors 166, one or more medication temperature sensors 168, all of which are electrically connected (either directly or indirectly) to an intelligent control 170. The medication temperature sensors 168 may include an ambient temperature sensor so that instead of directly measuring temperature of the medication, ambient temperature is measured and associated with the medication. The intelligent control 170 may be a circuit, a processor, a microcontroller, or other type of intelligent control. The intelligent control 170 is also electrically connected to a display 172 and a short range transceiver or transmitter 174. The pen 160 communicates with an electronic device such as, but not limited to either a cell phone 176 or computer 178. If a dose is missed, the pen could use the phone number or e-mail the user to remind them a dose is imminent. The electronic device may also be a medical device, or other type of electronic device. The short range transceiver 174 allows for information obtained from the sensors 162, 164, 166, 168 to be communicated to other devices for storage or analysis.

It should be understood that the intelligent control 170 may be configured to perform a number of intelligent operations or functions. For example, the intelligent control 170 may be configured to monitor the temperature of the medication and if the temperature of the medication falls above or below critical thresholds, alert the user that the medication is not safe and effective to use. The intelligent control 170 may be configured to monitor the state of various sensors over time and provide appropriate alerts or record sensed information. The intelligent control 170 may be configured to control audio associated with the use of the medication injection system such as to provide verbal acknowledgements or instructions such as, but not limited to "Injection complete", "Replace cartridge", "Apply additional pressure", and other acknowledgements or instructions which assist the user. The intelligent control 170 may also be configured to control simple beeps or other audio alerts or visual indicators in addition to the display, such as LEDs. Using the sensors, and preferably a clock component which may be integrated into the intelligent control 170, the intelligent control 170 can determine information regarding distribution, time of distribution and depth of injection attained, or other parameters as well as provide audible or visual reminders for distribution of the drug and feedback. Such information may be provided to other electronic devices.

The pen body may include various mechanical or electromechanical configurations for holding multiple needles and for removing needles from a needle array, or arrays, coupling the needle in place for rejection, extending the needle for injection, retracting the needle after injection, decoupling the now used needle and moving the now used needle back into the needle array.

Figure 5A:
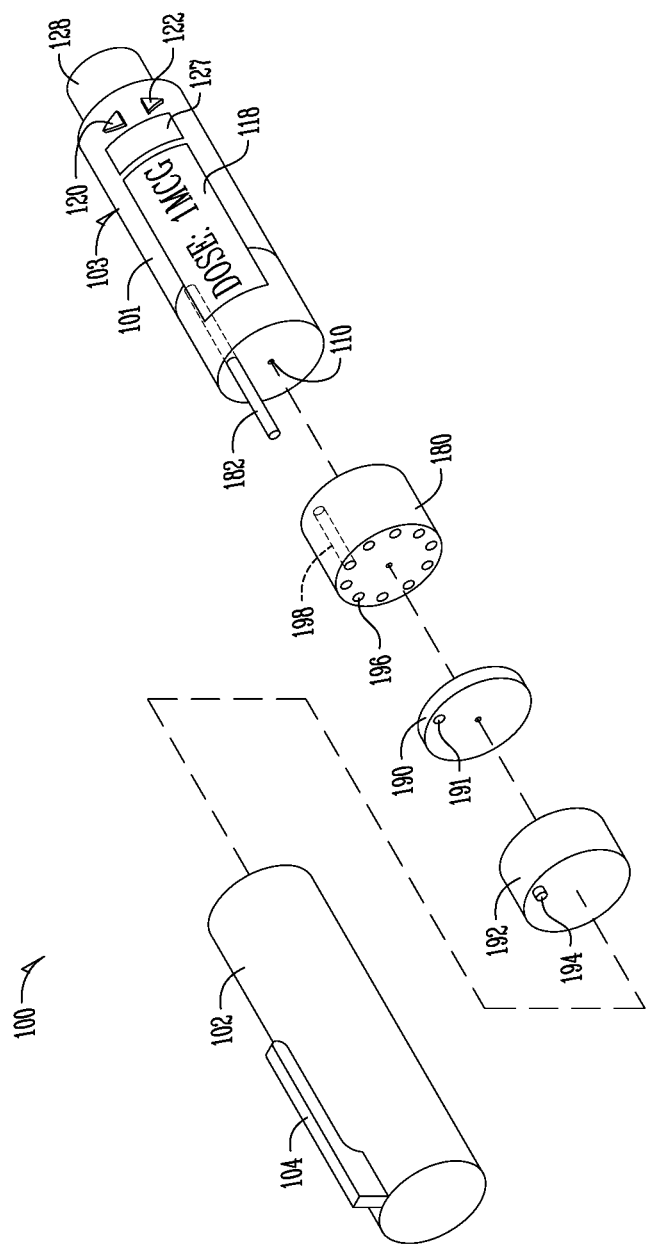
FIGS. 5A and 5B show one configuration for a medication delivery pen.
Figure 5B:
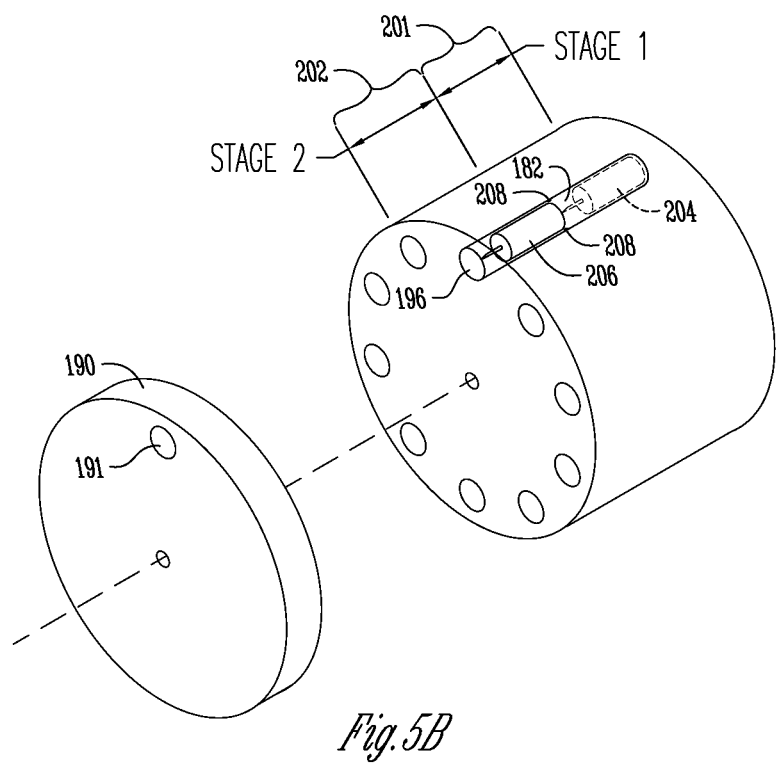

FIGS. 5A and 5B show one configuration. In FIG. 5A, a cylinder 180 contains a plurality of needles. The cylinder 180 is double staged. In the first stage, the cartridge connect 182 on cartridge 103 is coupled to the needle 204 as the cartridge 103 and cartridge connect 182 are moved from a neutral position to the first stage by depressing activation input 128. In the second stage of extension, the cartridge 103 and cartridge connect 182 with the coupled needle 204 are moved out of the cylinder 180 through the cover plate bore 191 in the cover plate 190 and the end cap bore 194 in the end cap 192 thereby exposing the needle for use. An antiseptic reservoir 127 may be used to apply an antiseptic or sterilizing solution prior to injection or after transfer of the used needle.

In the first stage of retraction, the needle 204 is retracted back into the cylinder bore 196 by depressing activation input 128. Then in the second stage of retraction, the needle 204 is decoupled from the cartridge connect 182. The needle 204 may be decoupled from the cartridge connect 182 by a detent 208 within the cylinder bore 196 that snags a catch on the needle 204. Alternatively, an oversized gasket/grommet could be positioned within the cylinder bore 196 which permits the needle 204 to move from stage 1 to stage 2, but decouples the needle 204 from the cartridge connect 182 when the needle 204 is moved from stage 2 to stage 1.

To rotate the cylinder 180 and align a new needle 204 with the cartridge connect 182, the activation input 128 is depressed. The rotation of the cylinder 180 may be either manual or automatic. Similarly, the cylinder 180 could be rotated to align a clean needle 204 with cartridge connect 182 during stage 2 after the cartridge connect 182 is decoupled from the used needle 204 and withdrawn from the cylinder 180. Alternatively, the cylinder 180 could be rotated to align a clean needle 204 with cartridge connect 182 at the outset of stage 1 upon extension of the cartridge connect 182, but prior to movement of the cartridge connect 182 into the cylinder 180. Upon rotation of the cylinder 180, the used needle 204 is then secured within the cylinder bore 196 at stage 2 between the detent 208 and the cover plate 190. Similarly, when all clean needles 204 within the cylinder 180 have been used, the cylinder 180 may align the cover plate bore 191 between two cylinder bores 182 to keep used needles 204 from passing through the cover plate bore 191 to thereby prevent exposure or reuse of the used needles 204. In another embodiment, the detent 208 or oversized gasket/grommet could be adapted to lock the used needle 204 in stage 2 of the cylinder 180 so that the used needle could not be advanced despite depression of the activation input 128. Thus, used needles can not be reused. Once the cylinder 180 is full of used needles 204, the user can safely dispose of the cylinder 180 and reload the medication delivery pen 100 with a new cylinder 180 with clean needles 204. The number of needles present should be related to the amount of medication, so that in some instances both will be depleted at or about the same time. Alternatively, if 180 and 103 are built as a single unit, the unit can be disposed of entirely.

Figure 5C:
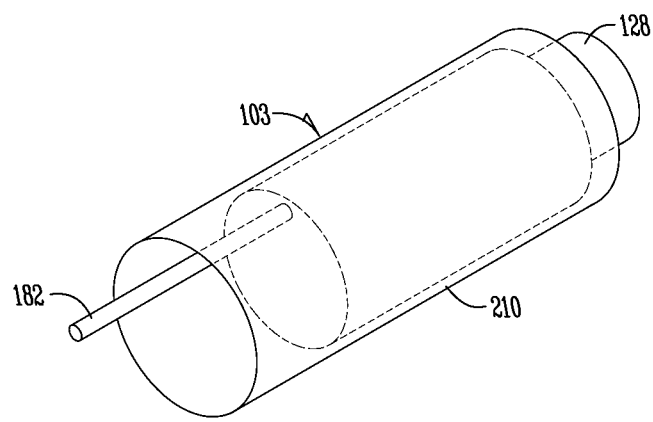
FIG. 5C illustrates the cartridge portion of a medication delivery pen.

FIG. 5C illustrates one embodiment of the cartridge portion 103 of the medication delivery pen 100. In this embodiment, the cartridge connect 182 extends from the cartridge 103. The cartridge 103 contains a reservoir of medication. Thus, when medication is depleted, the cartridge 103 can be replaced.

As previously explained, either a mechanical or electromechanical system may be used. The activation button 128 may be operatively connected a double action plunger. When the activation button 128 is pressed a first time, the cartridge 103 moves the cartridge connect 182 into the first stage within the cylinder 180 for coupling to the needle 204. The activation button 128 may then be depressed again to move the cartridge 103 with the cartridge connect 182 coupled to the needle 204 out of the end cap 192 to the second stage for injection. A third click then retracts the needle 204 to the second stage, detaches it from the cartridge connect 182, moves the cartridge connect 182 through the first stage into the neutral position, and rotates the cylinder 180 so that the cartridge connect 182 is aligned with a clean needle 204 in an adjacent cylinder bore 196. The cartridge 103 may be biased toward a neutral position by a spring or other biasing means.

Figure 6A:
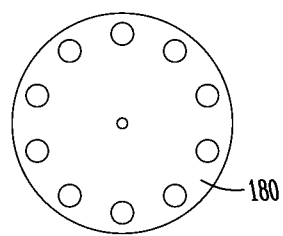
FIG. 6A to FIG. 6F illustrate a non-coupling embodiment where the needle is threaded onto the cartridge connect using a thumbwheel.
Figure 6B:
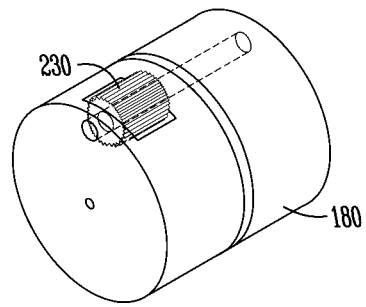
Figure 6C:
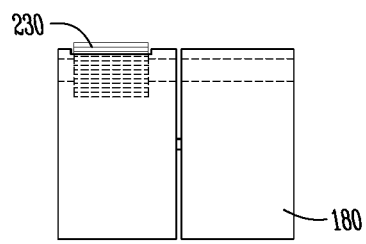
Figure 6D:
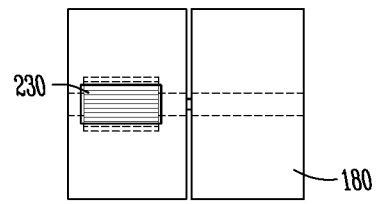
Figure 6E:
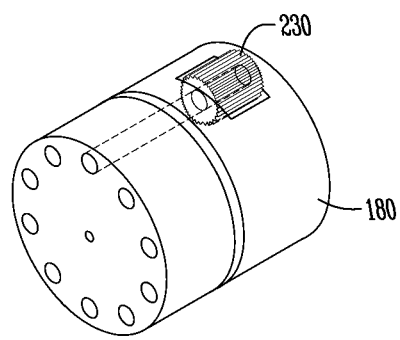
Figure 6F:
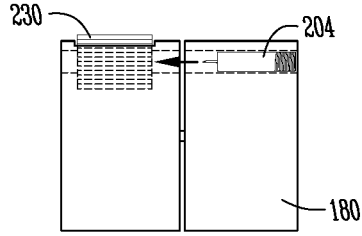

The embodiment shown in FIG. 5A through FIG. 5C attaches the needle 204 to the cartridge connect 182 using a quick coupler. The embodiment in FIG. 6A to FIG. 6G provides for a non-coupling embodiment where the needle 204 is threaded onto the cartridge connect 182. FIG. 6A shows an end view of the cylinder 180. FIG. 6B shows the cylinder 180 with a thumbwheel 230 on the outside of the cylinder 180. FIG. 6C is another view of the cylinder 180 with the thumbwheel 230 positioned over the cartridge connect 182. FIG. 6D is a top view of the cylinder 180. FIG. 6E is a perspective view of the cylinder 180 within the medication delivery pen 100, with the exterior surface of the medication delivery pen 100 having an opening to allow access to the thumbwheel 230. FIG. 6F illustrates a clean needle 204 in the cartridge connect which can be threaded in place through use of the thumbwheel. In operation, rotation of the thumbwheel 230 imparts rotation to the needle 204. A single thumbwheel 230 may be configured in the cylinder 180 for rotating/threading the clean needle 204 onto the cartridge connect 182.

Figure 7:
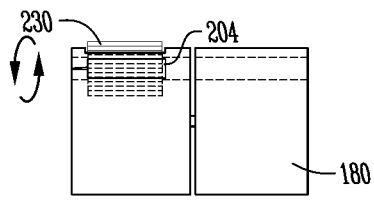
FIG. 7 illustrates a non-coupling embodiment where there are breaks in the bore so that a portion of the bore rotates separate from the rest of the bore.

FIG. 7 illustrates an alternative embodiment where breaks are in the cylinder bore 196 of the cylinder 180 so that a portion of the cylinder bore 196 rotates separate from the rest of the cylinder bore 196. The rotatable section of the cylinder bore 196 may be rotatably supported by needle bearings or ball bearings positioned on opposite ends of the rotatable section of the cylinder bore 196 so that rotation of the thumbwheel 230 imparts rotation to the freely rotatable cylinder bore 196 section, which rotates and threads the needle 204 onto the cartridge connect 182.

Figure 8A:
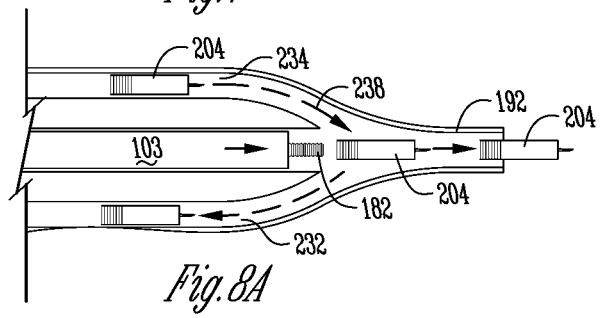
FIG. 8A is an embodiment which could incorporate either quick-connect, quick-coupling, manual, or automatic threading of the needle onto the cartridge connect.
Figure 8B:
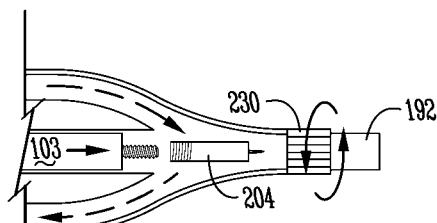
FIG. 8B-8E show a manually threaded embodiment
Figure 8C:
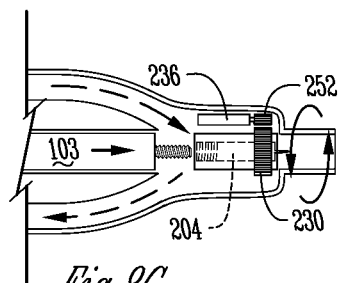
Figure 8D:
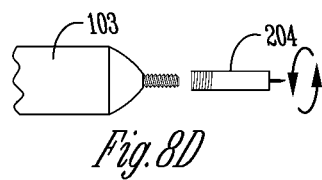
Figure 8E:
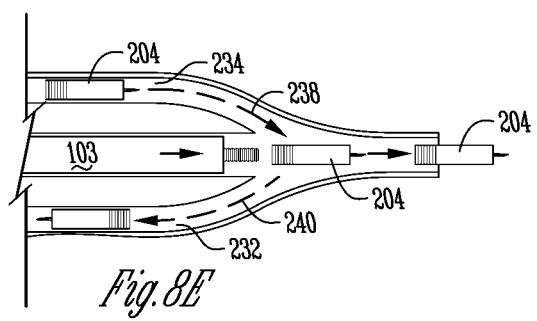

FIG. 8A is an alternative embodiment which could incorporate either quick-connect, quick-coupling, manual, or automatic threading of the needle 204 onto the cartridge connect 182. In the embodiment of FIG. 8A, note that the path of the needle 204 is connected from one side and disconnected from the other side. Thus, the used needles 204 are separated from the clean needles 204. FIG. 8B-8D shows this embodiment with a manually threaded embodiment (through operation of a thumbwheel 230). FIG. 8D illustrates how the needle cartridge may be a unitary piece with clean needles 204 on one side and used needles 204 on the opposite side.

In operation, in a first stage, a plunger moves the medicine cartridge connect 182 to couple or be threaded to a clean needle 204. In a second stage, the plunger moves the coupled/threaded needle 204 into the end cap 192 for use. In a third stage, the cartridge connect 182 retracts and decouples the now used needle 204 from the cartridge connect 182 or into the position to be unthreaded. If coupling is used, after the cartridge connect 182 is decoupled from the needle 204, the used needle 204 is ejected along arrow 240 from the loading stage into the used needle cartridge 232 and a new needle is moved from the clean needle cartridge 234 along arrow 238 into the loading stage. If threading is used, in the third stage, unthreading of the needle from the cartridge connect 182 takes place. In a fourth stage, movement (ejection) of the used needle from the loading stage into the used needle cartridge 232 occurs and new needle movement into the loading stage from the clean needle cartridge 234 occurs. The threading stage can be performed manually or by automatic operation. For example, a low-voltage servo motor 236 could be used to rotate thumbwheel 230 to thread and unthread needle 204 onto cartridge connect 182.

Figure 9A:
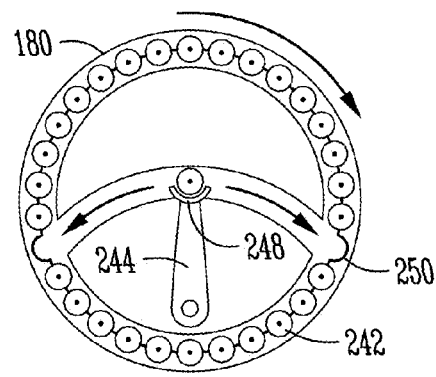
FIG. 9A-9D and FIG. 10 show an alternative embodiment of the medication delivery pen using a double-sided needle.
Figure 9B:
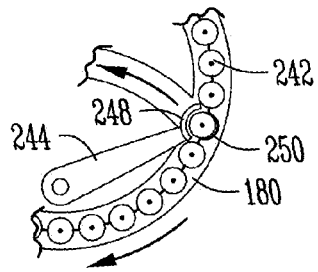
Figure 9C:
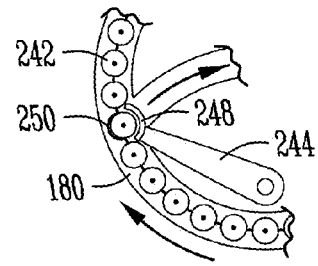
Figure 9D:
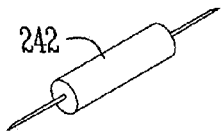
Figure 10:
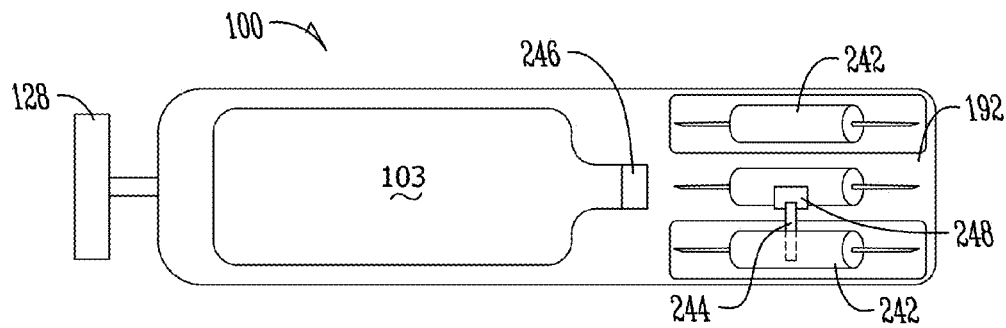

FIGS. 9A-D and 10 is another alternative embodiment of the medication delivery pen 100. FIG. 9A shows a cylinder 180 having a rotatable array of double-sided needles 242 (shown in FIG. 9D) carried by belt 250. Armature 244 is pivotably actuated, mechanically, electromechanically or otherwise, to sweep side-to-side within the cylinder 180. In one embodiment, armature 244 pivots toward belt 250 to pick up double-sided needle 242 using grip 248 positioned on the armature 244. In an alternative embodiment, each double-sided needle 242 could have a grip 248 that quick-couples to the armature 244 to pick up a clean double-sided needle 242 from the belt 250 (shown in FIG. 9B) and de-couples from the armature 244 to release the used double-sided needle 242 in the same or another position on the belt 250 (shown in FIG. 9C).

FIG. 9A-D and FIG. 10 show a double-sided needle 242 in the neutral position. In the neutral position, the double-sided needle 242 is ready for use. Depressing the activation button 128 causes the cartridge 103 or the cylinder 180 to move together whereby one of the needle spikes of the double-sided needle 242 is inserted into the needle valve 246 on the cartridge 103. The medication delivery pen 100 then may be pressed against the skin whereby the double-sided needle 242 and cartridge 103 are then moved together to extend the other needle spike on the double-sided needle 242 out of the end cap 192 to puncture the skin at which point the medication delivery pen 100 dispenses the specified dosage from the cartridge 103 through needle valve 246 and double-sided needle 242 into the body. After delivery of the medication, the used double-sided needle 242 is drawn back inside the cylinder 180, withdrawn out of the needle valve 246, and moved by the armature 244 into a stored position in the belt 250. The armature 244 then picks up a clean double-sided needle 242 and moves it from the belt 250 to the neutral position within the cylinder 180 for subsequent use.

In addition to the embodiments provided herein, the present invention contemplates numerous additions, variations, options, and alternatives. For example, instead of a single needle being used, multiple needles may be used as a part of an injection. An alcohol skin preparation may be performed prior to injection with the medication delivery pen facilitating the antiseptic, through an antiseptic reservoir. Such cleaning may also occur after the used needle is brought back into the assembly through bore 110.

In one embodiment, multiple containers may be used so that a medication delivery pen can deliver more than one type of medication. In such an embodiment, multiple configurations may be used, such as the ring configuration shown where one ring may be placed outside of another ring or above or below another ring. In addition, a device such as a glucometer may be incorporated into the device. Where the glucometer is present, the intelligent control of the medication delivery pen can set the dosage level.

The preferred embodiments of the present invention has been set forth in the drawings and specification and although specific terms are employed, these are used in the generically descriptive sense only and are not used for the purposes of limitation. Changes in the formed proportion of parts as well in the substitution of equivalence are contemplated as circumstances may suggest or are rendered expedient without departing from the spirit and scope of the invention as further defined in the following claims.

What is claimed is:

1. A medication delivery pen, comprising:
a proximal end, and a single bore through the proximal end;
an elongated pen body assembly comprising a distal end,
a needle array containing a plurality of double-sided needles, each of the double sided needles being an elongated body having a proximal needle spike at one end and a distal needle spike at an opposite end and each of the plurality of double-sided needles fully contained within the pen body assembly before and after use during an injection, the needle array configured to replace each double-sided needle after each extension and retraction of the proximal needle spike through the bore during the injection;
a cartridge having a reservoir of medicine, the cartridge being fully contained within the pen body assembly, the cartridge further comprising a needle valve positioned proximate the distal needle spike; and
an actuator on the pen body for initiating the injection, whereby the actuator is adapted to cause relative movement of the cartridge and one of double-sided needles together whereby the distal needle spike of the one of the double-sided needles is inserted into the needle valve of the cartridge and the proximal needle spike extends through the single bore; and
wherein a fluid within the reservoir of medicine travels directly through one of the needles from the reservoir through the distal needle spike and exits through the proximal needle spike when delivering medicine through the medication delivery pen;
further comprising a short range transceiver operatively connected to the elongated pen body assembly; and
an intelligent control and a display, wherein the display is positioned on the pen body assembly and electrically connected to the intelligent control.

2. The medication delivery pen of claim 1 wherein the pen body assembly further comprises a dose setting for setting a desired dose of medication to be dispensed from the pen body.

3. The medication delivery pen of claim 2 wherein the dose setting comprises a dose setting knob.

4. The medication delivery pen of claim 1 further comprising an actuator button operatively connected to the actuator for activating the actuator.

5. The medication delivery pen of claim 1 further comprising a cap for covering the distal end of the pen body assembly.

6. The medication delivery pen of claim 1 further comprising at least one sensor operatively connected to the pen body assembly.

7. The medication delivery pen of claim 1 further comprising a speaker operatively connected to the elongated pen body assembly.

8. The medication delivery pen of claim 1 further comprising a pen cap with a clip removably attached to the pen body assembly over the proximal end of the pen body assembly.

9. A medication delivery pen, comprising:
an elongated pen body assembly comprising a distal end, a proximal end, and a single bore through the proximal end;
a cartridge having a reservoir of medicine, the cartridge being fully contained within the elongated pen body assembly, the cartridge comprising a needle valve;
a needle array containing a plurality of double-sided needles, each of the plurality of double-sided needles having a proximal needle spike and a distal needle spike, the medication delivery pen configured to replace each needle after each extension and retraction of a needle; and
a needle assembly adapted to convey clean needles of the needle array towards the proximal end of the pen body assembly for delivering medication via injection and to convey used needles towards the distal end of the pen body assembly such that the plurality of needles remain fully contained within the needle assembly before injection and after injection;
an actuator on the pen body for initiating the injection, whereby the actuator is adapted to cause relative movement of the cartridge and one of the double-sided needles whereby the distal needle spike of the one of the double-sided needles is inserted into the needle valve of the cartridge and then to cause the cartridge and the one of the double-sided needles to move together until the proximal needle spike extends through the single bore; and
wherein a fluid within the reservoir of medicine travels directly through one of the needles from the reservoir through the distal needle spike and exits through the proximal needle spike when delivering medicine using the medication delivery pen;
wherein the needle valve is positioned proximate the distal needle spike;
further comprising a short range transceiver operatively connected to the elongated pen body assembly; and
an intelligent control and a display, wherein the display is positioned on the pen body assembly and electrically connected to the intelligent control.

10. The medication delivery pen of claim 9 wherein the needle array comprises a used needle cylinder and a clean needle cylinder wherein the clean needles are stored in the clean needle cylinder and used needles are stored in the used needle cylinder.

11. The medication delivery pen of claim 9 wherein the needle assembly includes a coupling for coupling the needle in place for delivery of the medication.

12. The medication delivery pen of claim 9 further comprising at least one button electrically connected to the intelligent control for adjusting dosage of the medication.

13. The medication delivery pen of claim 9 wherein the pen body assembly comprises a skin contact area distal the bore.

14. The medication delivery pen of claim 13 wherein at least one sensor is mounted at the skin contact area.

15. The medication delivery pen of claim 14 further comprising the intelligent control electrically connected to the at least one sensor.

16. The medication delivery pen of claim 15 wherein the at least one sensor comprises a temperature sensor.

17. The medication delivery pen of claim 15 wherein the at least one sensor comprises at least one contact sensor.

18. The medication delivery pen of claim 17 wherein the at least one sensor comprises at least one pressure sensor.

19. The medication delivery pen of claim 9 wherein the short range transceiver is an ultra wideband transceiver.

20. The medication delivery pen of claim 9 wherein the intelligent control is electrically connected to the short range transceiver and at least one sensor electrically connected to the intelligent control such that the medication delivery pen is adapted to convey information determined from the at least one sensor to an additional electronic device.

21. The medication delivery pen of claim 20 wherein the at least one sensor comprises a medication temperature sensor.

22. The medication delivery pen of claim 20 wherein the at least one sensor comprises a sensor for determining dosage.

23. The medication delivery pen of claim 9 further comprising a speaker operatively connected to the elongated pen body assembly.

24. A medication delivery pen for self-administration of injections, comprising:
- an elongated medication delivery pen body assembly comprising a distal end, a proximal end, and a single bore through the proximal end;
- a needle array containing a plurality of double-sided needles fully contained within the pen body assembly before and after injection, the medication delivery pen configured to replace each double-sided needle after each extension and retraction of a needle, each of the double-sided needles being an elongated body having a proximal needle spike at a first end and a distal needle spike at an opposite end;
- a cartridge having a reservoir of medicine comprising insulin, the cartridge being fully contained within the pen body assembly, the cartridge comprising a needle valve; and
- an actuator on the pen body for initiating the injection, whereby the actuator is adapted to cause relative movement of the cartridge and one of the double-sided needles whereby the distal needle spike of the one of the double-sided needles is inserted into the needle valve of the cartridge and then cause movement of the cartridge and the one of the double-sided needles together until the proximal needle spike extends through the single bore; and
- wherein a fluid within the reservoir of medicine travels directly through one of the needles from the reservoir through the distal needle spike and exits through the proximal needle spike when delivering medicine through the medication delivery pen;
- wherein the needle valve is positioned proximate the distal needle spike;
- further comprising a short range transceiver operatively connected to the elongated pen body assembly; and
- an intelligent control and a display, wherein the display is positioned on the pen body assembly and electrically connected to the intelligent control.

25. The medication delivery pen of claim 24 further comprising a pen cap with a clip removably attached to the pen body assembly over the proximal end of the pen body assembly.

26. The medication delivery pen of claim 24 further comprising an activation button along the pen body assembly between the distal end and the proximal end, the medication delivery pen configured to extend the needle through the single bore upon activation of the activation button.

27. The medication delivery pen of claim 24 further comprising a wireless transceiver disposed within the medication delivery pen for remote communication with another device.

28. The medication delivery pen of claim 24 wherein the elongated medication delivery pen body assembly is cylindrical.

29. A medication delivery pen, comprising:
- a pen body comprising a distal end, a proximal end, and a single bore through the proximal end;
- a cartridge having a reservoir of medicine comprising insulin, the cartridge being fully contained within the pen body, the cartridge comprising a needle valve;
- a plurality of double-sided needles, each of the double-sided needles having a proximal needle spike and a distal needle spike; and
- an actuator on the pen body for initiating the injection, whereby the actuator is adapted to cause relative movement of the cartridge and one of the double-sided needles towards each other whereby the distal needle spike of the one of the double-sided needles is inserted directly into the needle valve of the cartridge without passing through a connector and the proximal needle spike extends through the single bore; and
- wherein the pen body being configured to store each of the plurality of double-sided needles fully within the pen body both before and after use during injection;
- wherein a fluid within the reservoir of medicine travels directly through one of the double-sided needles from the reservoir through the distal needle spike and exits through the proximal needle spike when delivering medicine from the medication delivery pen;
- wherein the needle valve is positioned proximate the distal needle spike;
- further comprising a short range transceiver disposed within the pen body assembly; and
- an intelligent control electrically connected to the short range transceiver and at least one sensor electrically connected to the intelligent control such that the medication delivery pen is adapted to convey information determined from the at least one sensor to an additional electronic device.

30. The medication delivery pen of claim 29 further comprising a needle array, the plurality of double-sided needles contained in the needle array.

31. The medication delivery pen of claim 30 wherein the needle array comprises a used needle cylinder and a clean needle cylinder wherein clean needles are stored in the clean needle cylinder and used needles are stored in the used needle cylinder.

32. The medication delivery pen of claim 29 further comprising a coupling for coupling one of the plurality of needles in place for each delivery of the medication.

33. The medication delivery pen of claim 29 further comprising a display, wherein the display is positioned on the pen body and electrically connected to the intelligent control.

34. The medication delivery pen of claim 33 further comprising at least one button electrically connected to the intelligent control for adjusting dosage of the medication.

35. The medication delivery pen of claim 29 wherein the pen body comprises a skin contact area distal the bore through which one of the plurality of needles extends to deliver the medicine.

36. The medication delivery pen of claim 29 wherein at least one sensor is mounted at the skin contact area.

37. The medication delivery pen of claim 36 wherein the at least one sensor comprises a temperature sensor.

38. The medication delivery pen of claim 36 wherein the at least one sensor comprises at least one contact sensor.

39. The medication delivery pen of claim 36 wherein the at least one sensor comprises at least one pressure sensor.

40. The medication delivery pen of claim 36 wherein the at least one sensor comprises a medication temperature sensor.

41. The medication delivery pen of claim 29 wherein the short range transceiver is an ultra wideband transceiver.

42. The medication delivery pen of claim 29 further comprising at least one sensor for determining dosage.

* * * * *